(12) United States Patent
Greenway et al.

(10) Patent No.: US 8,497,070 B2
(45) Date of Patent: Jul. 30, 2013

(54) ANGIOGENIN MUTATIONS AND AMYOTROPHIC LATERAL SCLEROSIS OR MOTOR NEURON DISEASE

(75) Inventors: Matt Greenway, Dublin (IE); Orla Hardiman, Dublin (IE)

(73) Assignee: Royal College of Surgeons in Ireland, Dublin (IE)

( * ) Notice: Subject to any disclaimer, the term of this patent is extended or adjusted under 35 U.S.C. 154(b) by 450 days.

(21) Appl. No.: 12/701,790

(22) Filed: Feb. 8, 2010

(65) Prior Publication Data

US 2011/0123995 A1 May 26, 2011

Related U.S. Application Data

(60) Division of application No. 11/805,246, filed on May 22, 2007, now Pat. No. 7,659,243, which is a continuation-in-part of application No. PCT/IE2005/000131, filed on Nov. 22, 2005.

(30) Foreign Application Priority Data

Nov. 22, 2004 (GB) .................................. 0425625.1

(51) Int. Cl.
*C12Q 1/68* (2006.01)
*A61K 49/10* (2006.01)
*A61K 31/711* (2006.01)

(52) U.S. Cl.
USPC .......................................... 435/6.12; 424/9.1

(58) Field of Classification Search
None
See application file for complete search history.

(56) References Cited

U.S. PATENT DOCUMENTS

| | | |
|---|---|---|
| 6,706,871 B1 | 3/2004 | Ballinger et al. |
| 2008/0045456 A1 | 2/2008 | Greenway et al. |

OTHER PUBLICATIONS

Online Mendelian Inheritance in Man (OMIM) results for ANG gene <online>. Retrieved from: <http://omim.org/entry/105850> Retrieved on Mar. 28, 2012.*
Cronin et al., *Neurobiology* 67:1833-1836, Nov. 2006.
Del Bo et al., *Neurobiology of Aging* 29(2):314-316, Epublished Nov. 17, 2006.
Distler, J.H.W. et al., "Angiogenic and angiostatic factors in the molecular control of angiogenesis," *The Quarterly Journal of Nuclear Medicine* Sep. 2003; 47(3):149-161.
Greenway, M.J. et al., "A novel candidate region for ALS on chromosome 14q11.2," *Neurology* Nov. 23, 2004; 63(10):1936-1938.
Greenway, M.J. et al., "Angiogenesis and ALS: Screening of a novel candidate gene in the Irish ALS population," *Neurology* Apr. 2004; 62(7) Suppl. 5, p. A38.
Hayward, C. et al., "Molecular Genetic Analysis of the Apex Nuclease Gene in Amyotrophiclateral Sclerosis," *Neurology* Jun. 19, 1999; 52(9):1899-1901.
Itzeck J., *Acta Clin Croat* 47(2):77-79, Jun. 2008.
Lambrechts, D. et al., "VEGF: necessary to prevent motoneuron degeneration, sufficient to treat ALS?" *Trends in Molecular Medicine* Jun. 2004; 10(6):275-282.

\* cited by examiner

*Primary Examiner* — Daniel E Kolker
*Assistant Examiner* — Stacey N MacFarlane
(74) *Attorney, Agent, or Firm* — Wolf, Greenfield & Sacks, P.C.

(57) ABSTRACT

The invention relates to the use of angiogenin, or a fragment or variant thereof, to treat diseases or conditions characterized by neuronal injury or death, or axonal degeneration, especially neurodegenerative diseases such as Amyotrophic Lateral Sclerosis (ALS). The invention also describes a plurality of mutations of the human angiogenin gene which are associated with a neurodegenerative disease phenotype, and particularly a ALS phenotype. Also described is a method of assessing whether an individual is afflicted with, or generically predisposed to develop, a disease or condition characterized by neuronal injury or death, or axonal degeneration.

13 Claims, 7 Drawing Sheets

ANGIOGENIN MUTATIONS AND AMYOTROPHIC LATERAL SCLEROSIS OR MOTOR NEURON DISEASE

RELATED APPLICATIONS

This application is divisional of U.S. application Ser. No. 11/805,246, filed May 22, 2007, which was a continuation-in-part of and claims the benefit under 35 U.S. C. §120 of international application PCT/IE2005/000131, filed Nov. 22, 2005, which was published under PCT Article 21(2) in English.

INCORPORATION BY REFERENCE

This application incorporates by reference the Sequence Listing material in the ASCII text file filed on Feb. 8, 2010, entitled "P079770007US01-SEQ-TXT.txt", which file was created on Feb. 8, 2010, the size of which file is 18302 bytes.

TECHNICAL FIELD

The invention relates to a method of treating or preventing a disease or condition characterized by neuronal injury or death, or axonal degeneration, especially amyotrophic lateral sclerosis (ALS). The invention also relates to a method of assessing whether an individual is afflicted with ALS. The invention also provides a number of ALS specific mutations.

BACKGROUND OF THE INVENTION

ALS is paradigmatic of neurodegeneration and is the commonest neurodegenerative disorder of young and middle aged adults. The incidence of ALS in Ireland is 2.6/100,000. 10% of patients with ALS have a family history with an autosomal dominant pattern of inheritance and gain-of-function mutations in the SOD1 gene account for 20% of these. Although the pathogenesis is unknown, there is evidence that genetically determined susceptibility factors may contribute to the development of both ALS and other non-familial neurodegenerative diseases.

Mice with deletions of the hypoxia responsive element (HRE) of vascular endothelial growth factor (VEGF) have a 40% reduction in neural expression and adult-onset motoneuron degeneration, resembling an ALS phenotype. In addition to its angiogenic properties, VEGF has direct neurotrophic and neuroprotective effects on motoneurons and other central neurons. These observations suggest that insufficient VEGF dependent neurotrophic support may be of importance in the pathogenesis of ALS in this animal model.

Genotype meta-analysis of over 1,900 individuals from Northern Europe has identified a relative risk of 1.8 for the development of ALS in subjects homozygous with respect to two haplotypes in the VEGF promoter/leader sequence. The at-risk haplotypes reduce VEGF transcription and result in lowered serum VEGF levels. To date, no mutations in the VEGF HRE or coding sequences have been identified in patients with ALS, and the significance of low circulating VEGF levels remains to be determined.

The only evidence based treatment developed to date for ALS is riluzole, which extends life expectancy by approximately 3 months. The survival effect of riluzole wanes within 18 months of treatment.

SUMMARY OF THE INVENTION

It is an object of the invention to overcome at least one of the above problems. Accordingly, the invention relates to a method of treating or preventing a disease or condition characterized by neuronal injury or death, or axonal degeneration. The method of the invention comprises a step of treating an individual with angiogenin protein, or a neuroprotective fragment or variant thereof. Suitably, the angiogenin, or variant or fragment thereof, is administered in an amount effective to treat or prevent the disease or condition. When the invention relates to therapy, as opposed to prophylaxis, the individual is generally one in need of such treatment. Suitably, the disease or condition is a neurodegenerative disease, typically ALS or motor neuron disease, or variants thereof including primary lateral sclerosis and spinal muscular atrophy.

The invention also relates to angiogenin, or a neuroprotective fragment or variant thereof, for use as a medicament. Suitably, the medicament is for treating or preventing neurodegenerative disease, especially ALS or motor neuron disease, or variants thereof including primary lateral sclerosis and spinal muscular atrophy.

The invention also relates to the use of angiogenin, or a neuroprotective fragment or variant thereof, or a nucleic acid molecule encoding angiogenin or a fragment or variant thereof, in the manufacture of a medicament for the treatment or prevention of a disease or condition characterized by neuronal injury or death, or axonal degeneration. In particular, the invention relates to the use of angiogenin, or a neuroprotective fragment or variant thereof, or a nucleic acid molecule encoding angiogenin or a fragment or variant thereof in the manufacture of a medicament for the treatment or prevention of ALS or motor neuron disease, or variants thereof including primary lateral sclerosis and spinal muscular atrophy.

The Applicant has identified a number of variations in the angiogenin gene which have been shown to be associated with ALS. These variations will be hereafter referred to as mutations. Accordingly, the invention also relates to an isolated nucleic acid molecule comprising a nucleic acid sequence selected from the group comprising: SEQ ID NOs: 1 to 7. Each of the sequences is the sequence of a mutated form of the gene. The sequences as provided include a stop codon (taa), however, this may be excluded. Further, the sequences include coding for the signal peptide (Nucleotides 1-72), however sequences identical to SEQ ID NOs: 1 to 7 but excluding coding for the signal peptide (Nucleotides 1-72) also form part of the invention.

Polypeptide sequences corresponding to the mutant forms of the gene are also provided. Thus, in a further aspect, the invention relates to an isolated polypeptide comprising an amino acid sequence selected from the group comprising: SEQ ID NOs: 8 to 14. The amino acid sequences as provided in the Sequence Listing include the signal peptide (MVMGLGVLLLVFVLGLGLTP; SEQ ID NO: 18). However, the invention also relates to an isolated polypeptide comprising an amino acid sequence identical to one of SEQ ID NO'S 1 to 7 but without the signal peptide.

Specific details of the mutations in the angiogenin gene, and the resultant amino acid change in the mutant polypeptide, are provided in Table 1.

The invention also relates to a method of assessing whether an individual is afflicted with, or genetically predisposed to develop, a disease or condition characterized by neuronal injury or death, or axonal degeneration, the method comprising the step of assaying a biological sample from the individual for the presence of any of the mutations indicated in Table 1. The invention also relates to a kit for assessing whether an individual is afflicted with, or genetically predisposed to develop, a disease or condition characterized by neuronal injury or death, or axonal degeneration, the method comprising means for assaying a biological sample from the individual for the presence of any of the mutations indicated in Table 1. Typically, the means for assaying comprises an oligonucleotide probe or primer of the invention.

The invention also relates to a method of assessing whether an individual is afflicted with, or genetically predisposed to develop, a disease or condition characterized by neuronal injury or death, or axonal degeneration, the method comprising a step of comparing:

determining a serum level of circulating angiogenin in a sample obtained from the individual; and comparing the serum level of circulating angiogenin in the individual with a pre-determined range of control angiogenin levels, wherein a decreased serum level of angiogenin in the individual compared with the pre-determined control range is an indication that the individual is either afflicted with, or genetically predisposed to develop, a disease or condition characterized by neuronal injury or death, or axonal degeneration. Typically, the pre-determined control range is obtained from a cohort of individuals not afflicted, or genetically predisposed to develop, a disease or condition characterized by neuronal injury or death, or axonal degeneration. In a preferred embodiment, this diagnostic or prognostic method is specifically directed to the diagnosis or prognosis or neurodegenerative disease, especially ALS or motor neuron disease, or variants thereof including primary lateral sclerosis and spinal muscular atrophy. While this method of diagnosis/prognosis is defined in terms of measurement of serum levels of circulating angiogenin, it will be appreciated that the method may also be embodied by measurement of angiogenin levels in other biological fluids such as whole blood, lymph, cerebrospinal fluid, urine, saliva, semen etc.

Typically, the serum level of circulating angiogenin is determined using an ELISA test. One such test is commercially available under the trade name QUANTIKINE (R&D Systems, Minneapolis, Minn. 55413, USA) under Catalog No. DAN00.

The invention also relates to a kit for determining the serum level of circulating angiogenin in an individual, for use in assessing whether an individual is afflicted with neurodegenerative disease, or genetically predisposed to develop a neurodegenerative disease. Typically, the neurodegenerative disease is ALS or motor neuron disease, or variants thereof including primary lateral sclerosis and spinal muscular atrophy.

DETAILED DESCRIPTION OF THE INVENTION

The nucleic acid sequence of human angiogenin protein is provided in the NCBI database under Accession Number M11567. The sequence coding for the mature protein extends from nucleotide 1881 to 2249. The sequence of the mature protein, without the signal peptide, is provided below:

(SEQ ID NO: 15)
QDNSRYTHFLTQHYDAKPQGRDDRYCESIMRRRGLTSPCKDINTFIHGN

KRSIKAICENKNGNPHRENLRISKSSFQVTTCKLHGGSPWPPCQYRATA

GFRNVVVACENGLPVHLDQSIFRRP

The sequence of the full transcript, including the signal peptide, is provided in SEQ ID NO: 16, and the cDNA sequence of the human gene coding for the full transcript (mature protein plus signal peptide) is provided in SEQ ID NO: 17.

Generally, the angiogenin used in the methods and products of the invention will be human angiogenin in any of its documented isoforms. However, angiogenin obtained from, or based on, other mammalian angiogenin genes is included within the scope of the invention. Preferably, the angiogenin is recombinant angiogenin, most preferably recombinant human angiogenin. Recombinant human angiogenin is commercially available from R&D Systems Inc. (Minneapolis, USA) under Catalog Number 265-AN-250.

A "fragment" of the angiogenin protein means a contiguous stretch of amino acid residues of at least 5 amino acids, preferably at least 6 amino acids. Typically, the "fragment" will comprise at least 10, preferably at least 20, more preferably at least 30, and ideally at least 40 contiguous amino acids. In this regard, it would be a relatively straightforward task to make fragments of the protein and assess the neuroprotective activity of such fragments using the in-vitro or in-vivo models of motoneuron degeneration described below.

A "variant" of the angiogenin protein shall be taken to mean proteins having amino acid sequences which are substantially identical to wild-type angiogenin protein, typically human wild-type angiogenin. Thus, for example, the term should be taken to include proteins or polypeptides that are altered in respect of one or more amino acid residues. Preferably such alterations involve the insertion, addition, deletion and/or substitution of 5 or fewer amino acids, more preferably of 4 or fewer, even more preferably of 3 or fewer, most preferably of 1 or 2 amino acids only. Insertion, addition and substitution with natural and modified amino acids is envisaged. The variant may have conservative amino acid changes, wherein the amino acid being introduced is similar structurally, chemically, or functionally to that being substituted. Typically, angiogenin proteins which have been altered by substitution or deletion of catalytically-important residues will be excluded from the term "variant". Details of such catalytically-important residues will be well known to those skilled in the field of angiogenin protein modeling. Generally, the variant will have at least 70% amino acid sequence homology, preferably at least 80% sequence homology, more preferably at least 90% sequence homology, and ideally at least 95%, 96%, 97%, 98% or 99% sequence homology with wild-type angiogenin, typically mature wild-type human angiogenin (excluding the signal peptide as recited above). In this context, sequence homology comprises both sequence identity and similarity, i.e. a polypeptide sequence that shares 70% amino acid homology with wild-type human angiogenin is one in which any 70% of aligned residues are either identical to, or conservative substitutions of, the corresponding residues in wild-type human angiogenin. Specific variants included within the scope of the invention are the mutant angiogenin proteins identified in European Patent Publication Number 0 335 243, and ideally the mutant angiogenin proteins disclosed in U.S. Pat. No. 4,966,849. The contents of both of these documents, and the angiogenin mutants and variants disclosed therein, are incorporated herein by reference.

The term "variant" is also intended to include chemical derivatives of angiogenin, i.e. where one or more residues of angiogenin is chemically derivatized by reaction of a functional side group. Also included within the term variant are angiogenin molecules in which naturally occurring amino acid residues are replaced with amino acid analogues.

A fragment or variant of angiogenin will be considered to be "neuroprotective" when use of the fragment or variant in the in-vitro model of neurodegeneration described herein increases cell viability compared with a control.

Proteins and polypeptides (including variants and fragments thereof) of and for use in the invention may be generated wholly or partly by chemical synthesis or by expression from nucleic acid. The proteins and peptides of and for use in the present invention can be readily prepared according to well-established, standard liquid or, preferably, solid-phase peptide synthesis methods known in the art (see, for example, J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984).

The therapeutic method, and therapeutic products, of the invention are directed against diseases or conditions characterized by neuronal injury or death, or axonal degeneration. In one embodiment of the invention, the disease or condition characterized by neuronal injury or death, or axonal degeneration, is a neurodegenerative disease. Typically, the neurodegenerative disease is selected from the group comprising: motor neuron disease; prion disease; Huntington's disease; Parkinson's disease; Parkinson's plus; Tauopathies; Chromosome 17 dementias; Alzheimer's disease; Multiple sclerosis (MS); hereditary neuropathies; and diseases involving cerebellar degeneration. In a particularly preferred embodiment of the invention, the neurodegenerative disease is amyotrophic lateral sclerosis (ALS) or motor neuron disease, or variants thereof including primary lateral sclerosis and spinal muscular atrophy. The method of the invention is especially suited for treating or preventing ALS. The term "disease or condition characterized by neuronal injury or death, or axonal degeneration" should ideally be taken to exclude Central Nervous System (CNS) injury such as that caused by ischemia or trauma (i.e. stroke), and neurological complications associated with diabetes in a diabetic individual (i.e. diabetic neuropathy and diabetic retinopathy).

In a further embodiment, the disease or condition characterized by neuronal death is selected from the group comprising: multiple sclerosis (MS); epilepsy; schizophrenia; and diseases or conditions associated with inborn errors of metabolism.

In this specification the term "amount effective" should be taken to mean an amount which results in a clinically significant reduction or prevention of neuronal injury or death, or axonal degeneration. Suitably, the angiogenin or variant or fragment thereof, is administered at a dose of between 1 microgram and 10 milligrams per ml, preferably between 10 micrograms and 5 milligrams per ml, more preferably between 100 micrograms and 2 milligrams per ml. Typically, it is given as a bolus dose. However, when continuous infusion is used, such as by intrathecal pump, the protein, or fragment or variant thereof, may be administered at a dosage rate of between 5 and 20 µg/kg/minute, preferably between 7 and 15 µg/kg/minute. In the context of the therapeutic aspects of the present invention, the term "individual in need thereof" shall be taken to mean an individual who is afflicted with a disease or condition which involves neuronal degeneration or death, or axonal degeneration. Neurodegenerative diseases, such as ALS or motor neuron disease (also known as Lou Gehrig's disease), and variants thereof as described herein, are examples of such diseases.

In one embodiment of the invention, an individual in treated with angiogenin by direct delivery of the protein by a means selected from the group: intravenous delivery; oral delivery; intramuscular delivery; intrathecal delivery; and inhaled delivery. Methods for achieving these means of delivery will be well known to those skilled in the art of drug delivery. Specific examples are provided below:

Delivered intrathecally by mini-osmotic pump. (ref: Ignacio et al., Ann. N.Y. Acad. Sci. 2005, 1053: 121-136).

Intramuscular—Ang delivery directly into muscle(s) by syringe or mini osmotic pump (Azzouz et al., Nat. Med. 2005; 11(4):429-33).

Intraperitoneal—for systemic administration of Ang. Directly administered to peritoneum by syringe or mini osmotic pump (Kieran et al., Nat Med 2004; 10(4):402).

Subcutaneous—for systemic administration of Ang. Directly administered below the skin by syringe (Reinholz et al., Exp Neurol. 1999; 159(1):204-16).

Intraventricular—direct administration to the ventricles in the brain, by injection or using small catheter attached to an osmotic pump. (Sathasivam et al., 2005 Neuropath App Neurobiol; 31(5): 467)

Implant—ang can be prepared in an implant (e.g. small silicon implant) that will release ang. Implant can be placed at muscles or directly onto the spinal cord (Kieran and Greensmith, 2004 Neurosci 125(2):427-39).

In an alternative embodiment, the individual may be treated with angiogenin by transfecting the individual with an angiogenin expression vector, such as, for example, a viral vector. A suitable expression vector is a lentiviral vector. Typically, the angiogenin used in the methods of the invention is recombinant angiogenin. Methods for producing recombinant angiogenin, and expression vectors which express recombinant forms of the protein, will be well known to those skilled in the art (see for example Nature, Vol 429 (2004), P413-417 and Nature Medicine Vol 6 (2000) No 4 P405-413 and Azzouz et al., Nat. Med. 2005; 11(4):429-33) which describe methods of delivering recombinant VEGF to an animal model using a lentiviral expression vector. The gene therapy approach embodiment involves encoding ang and an attached marker protein (e.g. a fluorescent protein) in a virus, which will be administered to animals and taken up by cells whereby its incorporated into their genome and ang is expressed. (Currently the idea would be to over-express ang, and this would involve repeating ang sequence a number of times in the virus to produce a high copy number).

In one embodiment of the invention, the method includes a further step of treating the individual with VEGF, especially recombinant VEGF, protein. Thus, the invention also provides a medicament comprising angiogenin, or a neuroprotective fragment or variant thereof, and VEGF protein, or isoforms thereof. The invention also relates to the use the medicament of the invention in the manufacture of a medicament for the prevention or treatment of a disease or condition characterized by neuronal injury or death, or axonal degeneration, especially neurodegenerative diseases.

In one embodiment of the therapy of the invention, the angiogenin protein (or fragment or variant thereof) is linked to a coupling partner, e.g. an effector molecule, a label, a drug, a toxin and/or a carrier or transport molecule. Techniques for coupling the peptides of the invention to both peptidyl and non-peptidyl coupling partners are well known in the art.

As described above, the Applicant has also discovered a number of nucleotide sequence alterations (hereafter "mutations") in the gene for human angiogenin which are associated with neurodegenerative disease phenotype, especially ALS phenotype. The details of the gene mutations, and the corresponding mutations in the protein, are provided in Table 1 below.

TABLE 1

| SEQ ID NO (gene)* | Nucleotide Change** | Amino Acid Change*** | SEQ ID NO (protein) |
|---|---|---|---|
| 1 | A191T | K40I | 8 |
| 2 | A107T | Q12L | 9 |
| 3 | A122T | K17I | 10 |
| 4 | A121G | K17E | 11 |
| 5 | G164A | R31K | 12 |
| 6 | C189G | C39W | 13 |
| 7 | A208G | I46V | 14 |

*The sequences of the mutant angiogenin genes provided in SEQ ID NOs: 1 to 7 correspond with the coding for the full transcript of wild-type angiogenin (SEQ ID NO: 17), but include the mutations indicated above.
**The numbering used is calculated from the first nucleotide of the cDNA sequence encoding the full transcript (SEQ ID NO: 17).
***The numbering used is calculated from the first residue in the mature angiogenin peptide (SEQ ID NO: 15) provided above.

The nucleic acid sequence of the mutant genes (including coding for the signal peptide) are provided in SEQ ID NOs: 1 to 7. The amino acid sequence of the mutant proteins encoded by said mutant genes are provided in SEQ ID NOs: 8 to 14. The details of the disease-associated mutations are useful for designing nucleic acid probes or primers which may be used to detect the mutant forms of the genes in individuals. For example, a nucleic acid probe may be designed which binds specifically to a sequence of the gene which includes one or more of the mutations (i.e. it either binds specifically to the mutant gene and not to the wild-type gene, or it binds preferentially to the mutant gene as opposed to the wild-type). Typically, the probe will have a nucleic acid sequence which is complementary with a sequence of the gene which includes one or more of the mutations identified in Table 1. Suitably, the probe comprises a nucleic acid sequence which hybridizes under conditions of suitable stringency to at least 7, preferably at least 14, more preferably at least 25, 50, 75, 100, 150, 200, 250, 300, 350, or 400 consecutive nucleotides of the sequence of the angiogenin gene which includes at least one of the mutations.

Thus, in a further embodiment of the invention, there is provided an oligonucleotide which is complementary to a sequence of the angiogenin gene which includes at least one of the mutations indicated in Table 1. Typically, the oligonucleotide is a probe or a primer. Ideally, the primer is a primer for PCR nucleic acid amplification, ideally RT-PCR amplification. In one embodiment, the oligonucleotide consists of preferably at least 7, preferably at least 14, more preferably at least 25, 50, 75, 100, 150, 200, 250, 300, 350, or 400 consecutive nucleotides. The invention also relates to uses of the probes or primers of the invention in assessing whether an individual is affected with, or genetically predisposed to develop, a disease or condition characterized by neuronal injury or death, or axonal degeneration, especially neurodegenerative diseases such as ALS or motor neuron diseases, or variants thereof. For example, a sample of neuronal calls from an individual may be isolated, the DNA extracted, and then assayed using a probe of the invention for the presence of one of the mutations indicated in Table 1 Likewise, an oligonucleotide primer of the invention may be used to perform RT-PCR on the DNA sample. As the primer is designed to bind with the target DNA only when a desired mutation is present, amplification will only take place when the mutation is present. The design of primers and probes of the invention, and their use in determining the presence of any of the mutations of Table 1 in a sample, will be well known to a person skilled in the art.

The invention provides methods of treatment and prevention by administration to a subject in need of such treatment of a therapeutically or prophylactic ally effective amount of angiogenin, or a variant or fragment thereof (hereafter "therapeutic"). The subject is preferably an animal, including, but not limited to, animals such as monkeys, cows, pigs, horses, chickens, cats, dogs, etc., and is preferably a mammal, and most preferably human.

Apart from the specific delivery systems embodied below, various delivery systems are known and can be used to administer the therapeutic of the invention, e.g., encapsulation in liposomes, micro particles, microcapsules, recombinant cells capable of expressing the Therapeutic, receptor-mediated endocytosis (see, e.g., Wu and Wu, 1987, J. Biol. Chem. 262:4429-4432), construction of a therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example, by means of an implant, said implant being of a porous, non-porous, or gelatinous material, including membranes, such as silastic membranes, or fibers.

In another embodiment, the therapeutic can be delivered in a vesicle, in particular a liposome (see Langer, Science 249: 1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the therapeutic can be delivered in a controlled release system. In one embodiment, a pump may be used (see Langer, supra; Sefton, CRC Crit. Ref. Biomed., Eng. 14:201 (1987); Buchwald et al., Surgery 88:75 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

In a specific embodiment where the therapeutic is a nucleic acid encoding a protein therapeutic, the nucleic acid can be administered by gene therapy methods as described herein.

The present invention also provides pharmaceutical compositions comprising angiogenin, or a variant or fragment thereof. Such compositions comprise a therapeutically effective amount of the therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopoeia for use in animals, and more particularly in humans.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like.

The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to, ease pain at the, site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropyl amine, triethylamine, 2-ethylamino ethanol, histidine, procaine, etc.

The amount of the therapeutic of the invention which will be effective in the treatment of a particular disorder or condition will depend on the nature of the disorder or condition, and can be determined by standard clinical techniques. In addition, in vivo and/or in vitro assays may optionally be employed to help predict optimal dosage ranges. The precise dose to be employed in the formulation will also depend on the route of administration, and the seriousness of the disease or disorder, and should be decided according to the judgment of the practitioner and each patient's circumstances.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

EXAMPLES

Example 1

Genotyping Data

The Applicant has previously identified chromosome 14q11.2 as a candidate region for amyotrophic lateral sclerosis in the Irish and Scottish populations (Greenway, M. J. et al. *Neurology*. 63, 1936-1938 (2004) Hayward, C. et al *Neurology*. 52, 1899-901 (1999)) and have reported an association of ALS with the rs11701 single nucleotide polymorphism (SNP) in the Irish ALS population (Greenway, M. J. et al. *Neurology*.). Genotyping of the rs11701 SNP in 1629 individuals with ALS and 1264 controls from 5 independent populations (Table 2) confirmed the association in the Irish and Scottish ALS populations, although no association was observed in US, English or Swedish populations. The rs11701 SNP is a synonymous substitution in ANG, a one exon gene whose product is expressed in motor neurons, and is an angiogenic factor with RNase A activity.

Figure 1:
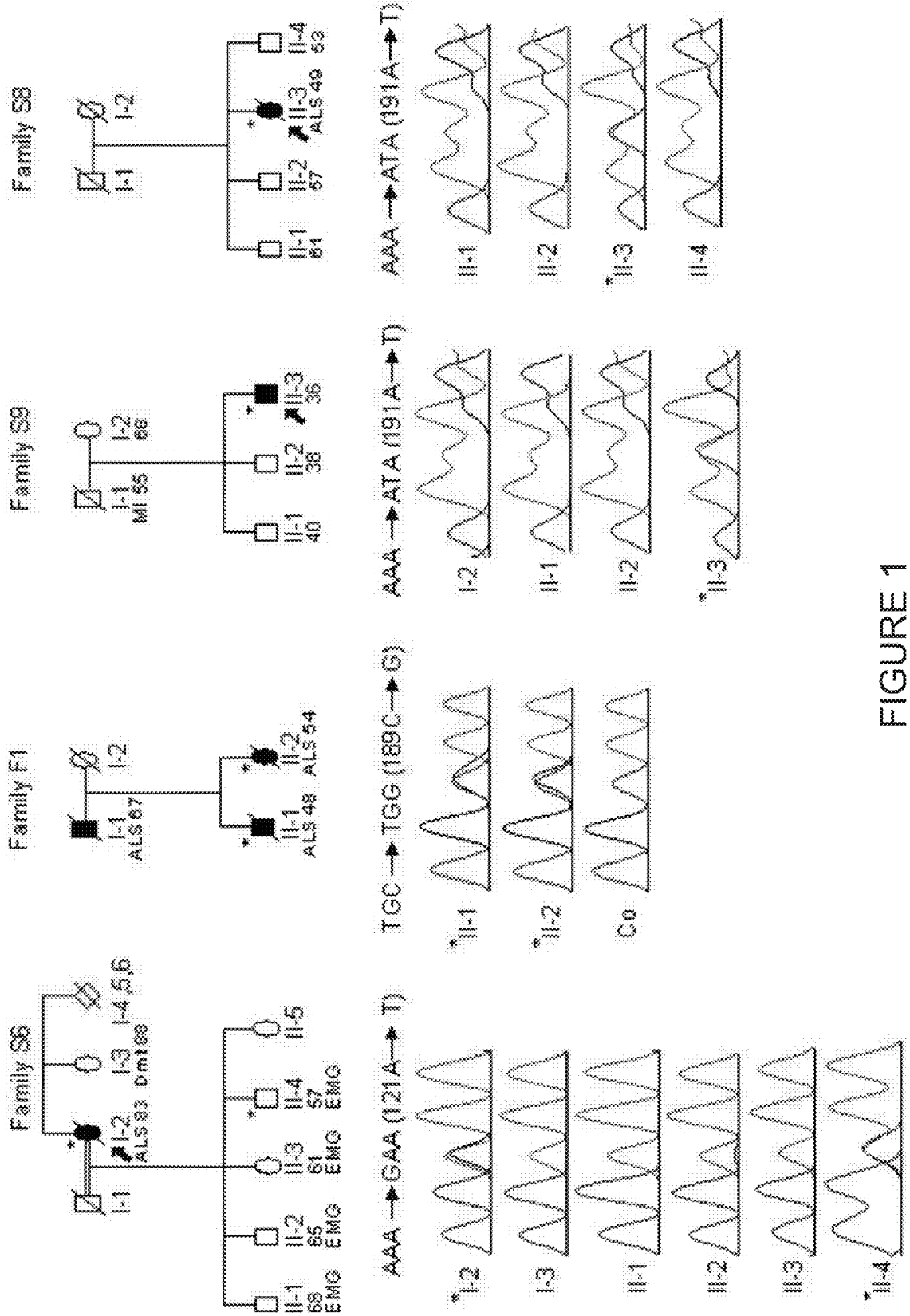
FIG. 1 shows the pedigrees for selected patients with ANG mutations. Mutations are indicated using single letter amino acid code. Probands are indicated by arrows, circle, female; square male; open symbol, unaffected; shaded symbol, affected; diagonal line, deceased; Co, control; asterisk, mutation. Current age, or age at death and cause of death, is indicated. Dmt, dementia; MI, myocardial infarction; EMG, normal electromyogram.

Sequencing of the human angiogenin gene (hereafter ANG) in the same populations identified 7 missense mutations in 15 individuals of whom 4 had familial ALS and 11 'sporadic' ALS, (Table 3). These individuals were all negative for super oxide dismutase 1 mutations. Although mutations were present in individuals from all 5 populations, 12 of 15 affected individuals were of Scottish or Irish descent (Table 3). To the Applicants knowledge ANG variants have not been previously associated with human disease. ALS-associated mutations were not identified in 2528 ethnically matched control chromosomes and segregated with disease in one family (FIG. 1.) All patients enrolled in the study had typical ALS, although a higher than expected proportion (60%) of individuals with ANG mutations had bulbar onset disease. However, specific mutations were not associated with site of onset, the C39W mutation was observed in two siblings one of whom had confirmed clinical features of limb onset and the other bulbar onset ALS.

TABLE 2

Clinical details of study populations

| Study Populations | Total | Male/ female | Mean age at onset (SD) | % Spinal onset | % Bulbar onset |
|---|---|---|---|---|---|
| Irish | | | | | |
| SALS | 262 | 142/120 | 57 (13.5) | 76 | 24 |
| FALS | 31 | 21/8 | 58 (8.9) | 71 | 29 |
| Population-based controls | 339 | 217/122 | 44 (12.5) | — | — |
| Scottish | | | | | |
| SALS | 364 | 212/152 | 55 (14.1) | 72 | 28 |
| FALS | 34 | 17/17 | 58 (14.8) | 76 | 24 |
| Population-based controls | 299 | 151/148 | 48 (11.6) | — | — |
| USA (Boston) | | | | | |
| SALS | 277 | 169/108 | 55 (13.0) | 77 | 23 |
| FALS | 83 | 36/47 | 53 (13.3) | 72 | 28 |
| Population-based controls | 219 | 74/140 | 54 (18.2) | — | — |
| Sweden | | | | | |
| SALS | 334 | 187/147 | 63 (15.1) | 70 | 30 |
| FALS | 100 | 51/49 | 62 (14.6) | 83 | 17 |
| Healthy spouses | 135 | 70/65 | 65 (13.8) | — | — |
| Neurological controls | 174 | 92/82 | 67 (13.6) | — | — |
| England (Birmingham) | | | | | |
| SALS | 133 | 84/49 | 61 (10.6) | 71 | 29 |
| FALS | 11 | 7/4 | 52 (16.3) | 73 | 27 |
| Population-based controls | 98 | 30/68 | 58 (12.2) | — | — |

TABLE 3

Clinical, ethnic and genetic characterization of individuals with ANG mutations

| Proband | Ethnic origin | Mutation in ANG | Amino acid substitution | Family History of ALS | Number affected in family | Age of onset in years | Site of onset | Survival in years |
|---|---|---|---|---|---|---|---|---|
| S1 | Scottish | A107T | Q12L | No | 1 | 48 | B | n/a |
| S2 | Irish/Scottish | A107T | Q12L | No | 1 | 75 | L | >7 |
| S3 | Irish/Scottish | A122T | K17I | No | 1 | 53 | L | n/a |
| S4 | Irish | A122T | K17I | No | 1 | 53 | L | n/a |
| S5 | Irish | A121G | K17E | No | 1 | 66 | B | >3 |
| S6 | Swedish | A121G | K17E | No | 1 | 83 | B | 0.8 |
| S7 | Irish/English | G164A | R31K | No | 1 | 66 | B | 1 |
| F1a | European | C189G | C39W | Yes | 3 | 45 | L | 4 |
| 1b | European | C189G | C39W | Yes | 3 | 47 | B | 7 |
| S8 | Irish | A191T | K40I | No | 1 | 45 | B | 4 |
| S9 | Irish | A191T | K40I | No | 1 | 27 | L | 10 |
| S10 | Scottish | A191T | K40I | No | 1 | 70 | B | 3 |
| S11 | Scottish | A208G | I46V | No | 1 | 76 | B | 1.5 |
| F2 | Scottish | A208G | I46V | Yes | n/a | 41 | B | 1.5 |
| F3 | Scottish | A208G | I46V | Yes | 2 | 45 | L | 12 | n/a = not available

Three shared haplotypes were observed across the ANG locus and flanking region in Irish and Scottish individuals with K17I (S3, S4), K40I (S8, S9 and S10) and I46V (S11, F2 and F3) mutations respectively, indicative of a founder effect in each case. A unique shared haplotype for the K17E mutation was identified in individuals of Swedish and Northern Irish ethnicity (S5 and S6).

ANG, a 123 amino acid 14.1 kDa protein, is a potent inducer of neovascularization in vivo and member of the pancreatic ribonuclease A (RNase A) superfamily (Fett, J. W. et al. *Biochem.* 24, 5480-5486 (1985)). The RNase activity of ANG is important for its biological activity (Shapiro, R., Riordan, J. F. & Vallee, B. L. *Biochem.* 25, 3527-3532 (1986)). ANG variants with decreased RNase activity invariably have reduced angiogenic activity (Shapiro, R., Fox, E. A & Riordan, J. F. *Biochem.* 28, 1726-1732 (1989); Shapiro, R & Vallee, B. L. *Biochem.* 28, 7401-7408 (1989)). ANG is expressed in the neuroaxis. However, its mechanism of action is yet to be established. In endothelium ANG organizes cell formation into tube-like structures, induces secondary messengers, and supports endothelial cell adhesion and spreading. In steps that are critical for angiogenesis, ANG is internalized by endothelial cells and transported to the nucleolus (Morioanu, J. & Riordan, J. F. *Proc. Natl Acad Sci USA.* 91, 1667-1681 (1994)) where it stimulates rRNA transcription, a rate-limiting step in ribosome biogenesis, protein translation and cell growth. Endogenous ANG is required for cell proliferation induced by other angiogenic proteins such as vascular endothelial growth factor (VEGF) (Kishimoto, K., Liu, S., Tsuji, T., Olson, K. A. & Hu, G. F. *Oncogene.* 24, 445-456 (2005) Downregulation of ANG by small interfering RNA (siRNA) and antisense oligonucleotides decreases VEGF-induced rRNA transcription and inhibition of nuclear translocation of ANG abolishes VEGF's angiogenic activity (Kishimoto, K., Liu, S., Tsuji, T., Olson, K. A. & Hu, G. F. *Oncogene.* 24, 445-456 (2005).

Figure 2:
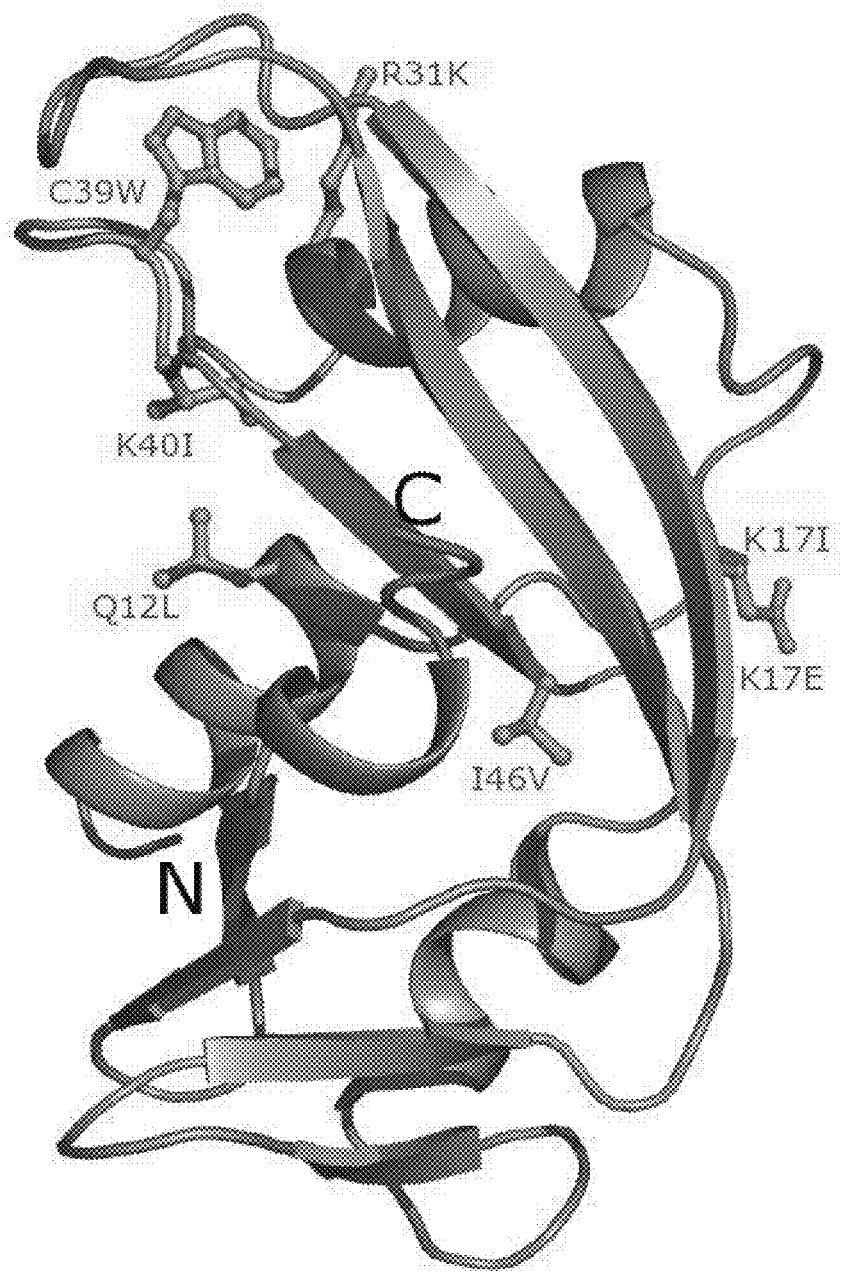
FIG. 2 illustrates the three-dimensional structure of ANG showing the modeled mutations: Q12L, K17E, K17I, R31K, K40I, and I146V: in ball and stick representation. The figure was created using the program PyMOL (DeLano Scientific, San Carlos, Calif.).

Crystal structure analysis of ANG has provided clear evidence of RNase A fold and conservation of H13, K40 and H114—the catalytic triad (Acharya, K. R., Shapiro, R., Allen, S. C., Riordan, J. F. & Vallee, B. L. *Proc. Natl. Acad. Sci. USA.* 91, 2915-2919 (1994). Five of the missense mutations identified in 11 individuals with ALS affect functionally important residues that are evolutionary highly conserved in ANG and RNase A (Q12L, K17I, K17E, C39W and K40I) (FIG. 2). K40 in ANG is a critical residue involved in catalysis (Shapiro, R., Riordan, J. F. & Vallee, B. L. *Biochem.* 25, 3527-3532 (1986)). Replacement of K40 by Q, or a conservative substitution by R, decreases the ribonucleolytic activity by a factor 2×10 (Fett, J. W. et al *Biochem.* 24, 5480-5486 (1985) and 50-fold respectively (Shapiro, R., Fox, E. A. & Riordan, J. F. *Biochem.* 28, 7401-7408 (1989). Without being bound by theory, molecular modelling of the K40I substitution suggests that several key interactions are lost due to mutation, predicting loss of ribonucleolytic activity (FIG. 2). C39W causes significant structural change due to loss of disulfide bridge formation with C92 (FIG. 2). Disruption of this disulfide bridge would likely affect protein folding resulting in lower ribonucleolytic activity. Q12 interacts with the active site residue K40 in the native structure (FIG. 2). Q12L substitution would disrupt this interaction and make it enzymatically less active. Residue K17 in ANG is distantly positioned from the active site in a loop on the surface of the molecule (FIG. 2). It is unlikely that variants K17 to I or E have significant effect on the structure. However, previous study on a ANG-RNase A hybrid demonstrates a conserved region containing K17 is involved in the activity of ANG against intact ribosomes. This suggests that I/E variants of K17 may alter ANG activity (Bond, M. D. & Vallee, B. L. *Biochem.* 29, 3341-3349 (1990).

In addition to the catalytic centre, ANG possesses a nuclear translocation site that contains sequence ($_{31}$RRRGL$_{35}$; SEQ ID NO: 19) involved in transport of ANG to the nucleolus following uptake by endothelial cells. R31A is translocated much less efficiently than the native protein (Shapiro, R. & Vallee, B. L. *Biochem.* 31, 12477-12485 (1992). It is predicted that the R31K variant may have a role in nuclear translocation but would cause only minor perturbation in the structure. I46 is not fully conserved and is predicted to cause the least structural change.

Like VEGF, ANG is induced by hypoxia to elicit angiogenesis and is expressed in motor neurons. Deletion of the hypoxic response element of the VEGF promoter causes a motor neuron disease phenotype in mice (Oosthuyse, B. et al. *Nat. Genet.* 28, 131-138 (2001)) and replacement of VEGF is beneficial in SOD$^{G93A}$ rodent models (Azzouz, M. et al. *Nature.* 429 413-417 (2004) Storkebam, E. et al *Nat Neurosci* 8, 85-92 (2005)). Gene-based therapy using a VEGF expressing lentiviral vector MoNuDin® is being developed for human use by Oxford Biomedica. Although VEGF is a putative modifier of ALS, mutations in the gene have not been found in patients with ALS. By contrast, the Applicant has identified loss of function ANG mutations as a clear susceptibility factor for the development of ALS. ANG mutations may cause autosomal dominant ALS and low penetrant disease masquerading as 'sporadic' ALS.

Example 2

Cell Model of Motoneuron Degeneration

Methods

Primary motoneuron cultures at 7 days in-vitro were exposed to 50 uM AMPA (Tocris Cookson) in the culture medium for 24 hrs, as an in-vitro model of motoneuron degeneration (Kieran and Greensmith, Neuroscience 2004, Vol. 125:427-439). To examine the possible neuroprotective effect of angiogenin we examined the effect of i) pre-treatment and ii) co-treatment with angiogenin (R&D Systems) in the culture medium at concentrations of 25 ng/ml, 50 ng/ml, 100 ng/ml, 200 ng/ml and 500 ng/ml. As controls, sister cultures were used that were either unexposed, or exposed to angiogenin (at same concentrations as detailed above), or exposed to BSA (bovine serum albumin, Sigma).

In this study an MTT cell viability assay was performed. MTT (Sigma) dissolved in PBS (5 mg/ml) and diluted 1:10 in culture medium was added to cultures and incubated for 4 hours at 37 C. After incubation, the media was replaced with isopropanol containing 0.04M HCl. Emission values were then read on a micro-ELISA plate reader at 570 nm. Cell viability in treated cultures was expressed as a percentage of cell viability in untreated sister cultures (100%) and results were compared for significance using a Mann Whitney U-test.

Figure 3:
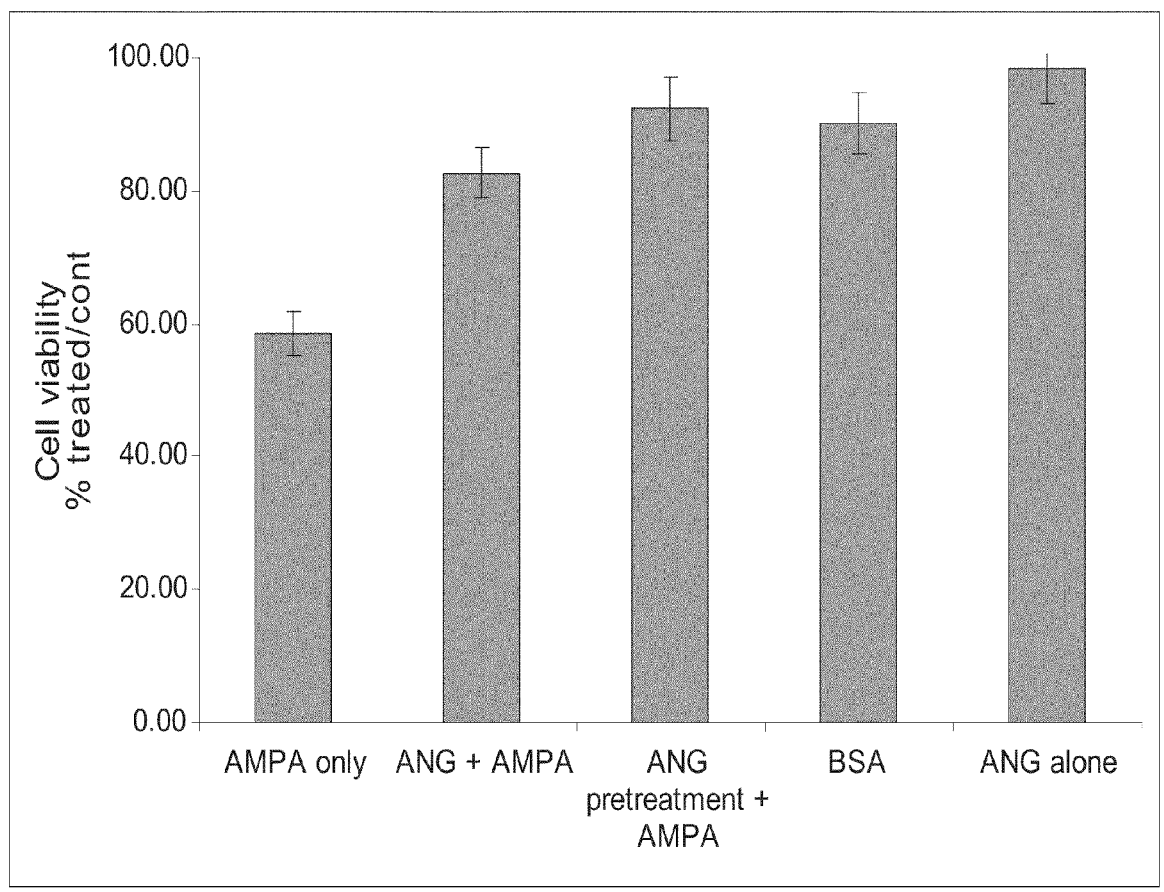
FIG. 3: MTT assay. An MTT assay was used to determine the neuroprotective effect of angiogenin treatment in an in-vitro model of motoneuron degeneration. Cell viability in treated cultures was expressed as a percentage of cell viability in untreated sister cultures (controls). As can be seen exposure to AMPA results in a significant decrease in cell viability, however co-treatment or pre-treatment with angiogenin (100 ng/ml) significantly increases cell viability. Exposure to angiogenin or BSA alone has no significant effect on cell viability. (values=mean, error bars=S.E.M., N=24).

To examine the signalling pathway involved in mediating the neuroprotective effect of angiogenin, the activation of the PI3K/Akt pathway was examined using western blotting. In particular, we examined the activation of Akt, as demonstrated by its phosphorylation. Primary motoneuron cultures exposed to AMPA, AMPA and angiogenin, or angiogenin alone (as described above) were lysed and protein extracted. Protein concentration in each experimental condition was determined using a Micro BCA Assay (Pierce). Samples were run on a 10% SDS gel and transferred onto nitrocellulose membranes, and were probed with antibodies to Akt and phospho-Akt (both Cell Signalling). Blots were visualised using the ECL system. Equal protein loading was confirmed by re-probing blots with antibodies to alpha-tubulin (Sigma).
Results 1. The Neuroprotective Effect of Angiogenin in an In-Vitro Model of Motoneuron Degeneration and STROKE.

a) Using an MTT cell viability assay the effect of increasing concentrations of angiogenin was examined in an in-vitro model of motoneuron degeneration where primary motoneuron cultures were exposed to 50 uM AMPA for 24 hrs. It was found that the optimum concentration of angiogenin to demonstrate a neuroprotective effect was 100 ng/ml. Exposure of primary motoneuron cultures to 50 uM AMPA for 24 hrs is a well described in-vitro model of motoneuron degeneration (Kieran and Greensmith, 2004). As can be seen in FIG. 3, exposure to AMPA results in a significant decrease in cell viability to 58.5% (+/−3.3 S.E.M., n=24, p=<0.05). However, co-treatment or pre-treatment with 100 ng/ml angiogenin significantly increased cell viability to 82.5 (+/−3.9 S.E.M., n=24) and 92.3% (+/−4.8 S.E.M., n=24), respectively (p=<0.05). Treatment of primary motoneuron cultures with either angiogenin or BSA had no significant effect on cell viability.

2. The Role of Akt in Angiogenin Signalling

Figure 4:
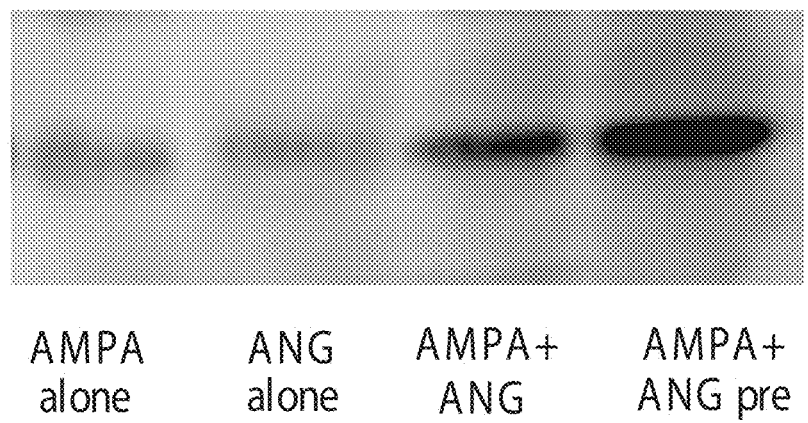
FIG. 4: Western blot for phosphorylated Akt. The activation of the PI3K/Akt pathway was examined by western blot for phosphorylated Akt. As can be seen there is a strong increase in phospho-Akt expression in AMPA exposed cultures co-treated or pre-treated with angiogenin. This suggests that the neuroprotective effect of angiogenin involves signalling through the PI3K/Akt signalling pathway.

Using western blotting, the cell survival pathways involved in mediating the neuroprotective effect of angiogenin were examined. In particular the activation of the PI3K/Akt cell survival pathway was examined by examining the expression of the active form of Akt (phosphorylated Akt). As can be seen in FIG. 4, the level of activated Akt (phosphorylated Akt) is increased in AMPA exposed cultures co-treated with angiogenin, compared to AMPA-only or angiogenin-only treated cultures. This increase in the activated form of Akt demonstrates that the neuroprotective effect of angiogenin in this in-vitro model of motoneuron degeneration involves the activation of the PI3K/Akt pathway.

Example 3

Animal Model of Neurodegeneration

Treatment Regimes:

Angiogenin (ang) (R&D Systems Inc., Minneapolis, USA—Catalog Number 265-AN-250) was administered to mutant SOD1 (mSOD1, SOD1$^{G93A}$) mice, a mouse model of ALS/MND (Gurney et al., 1994 Science 264:1772-5). These mice may be obtained from The Jackson Laboratory, Maine, USA. These mice develop an ALS-like phenotype of progressive motoneuron degeneration and hindlimb paralysis, which very closely mimics the clinical situation. The disease progresses rapidly in these mice, and they have a much reduced lifespan of approximately 125 days (Kieran et al., Nat Med, 10:402-5, 2004). The effect of commencing ang treatment at different disease stages is examined. These stages are i) pre-symptomatically (from 35-days), ii) early-symptomatic stage (from 70-days) or iii) late-symptomatic stage (from 90-days; this point most closely mimics the clinical situation as patients only see neurologist at mid-late stage i.e. when paralysis is evident). Angiogenin is administered to animals of the same sex from a number of litters, in order to prevent sex differences distorting the results.

Routes of Administration:

1. Intrathecal-Ang Delivery Directly to the Spinal Cord.

Animals have ang administered intrathecally by syringe. This involves exposing the spinal cord in anaesthetized animals by performing a laminectomy to create a 'hole' in the overlying vertebrae and then inserting the syringe through this hole, through the meninges into the space surrounding the spinal cord. The syringe will not penetrate the spinal cord.

Alternatively, the animals have ang delivered intrathecally by mini-osmotic pump. Animals are anaesthetized, and a laminectomy is performed to allow a small catheter to be inserted intrathecally. This catheter is attached to a mini-osmotic pump containing angiogenin. These pumps are very small in size and suitable for insertion into small rodents such as mice. The pump is located overlying the spinal cord, and ang is released over a defined length of time, depending on the size of the pump and the volume it can hold. (Ignacio et al., Ann. N.Y. Acad. Sci. 2005, 1053: 121-136).

In the situation that recombinant ang is to be administered, the effect of different concentrations is first examined and then the optimal delivery regime is examined (i.e. administered continuously (osmotic pump would allow for this), daily, twice daily, weekly, fortnightly, every other day etc.). For continuous infusion, recombinant angiogenin is infused at a range of doses between 5 and 20 µg/kg/minute. Otherwise, the angiogenin is administered at a range of doses between 0.1 and 2 mg/kg.

Determining Effectiveness of Treatment:

To determine whether Ang treatment is effective in mSOD1 mice, disease progression and lifespan in treated mSOD1 mice is compared with untreated mSOD1 littermates. Monitoring disease progression includes functional assessment of locomotor ability and muscle function, as well as body weight, general appearance and motoneuron survival. These methods are described in Kieran et al. (2005, 2004). Lifespan is a measure of the number of days the animal lives for.

Results:

Angiogenin is released from the pumps and syringe and taken up by cells in the spinal cord. This is monitored by tagging the Ang protein with a fluorescent marker. Administration of Ang directly to the spinal cord will reduce the possibility of Ang administration having carcinogenic effects, compared to systemic Ang administration.

Example 4

Evidence of the Neuroprotective Effect of Angiogenin In-Vivo

Figure 5:
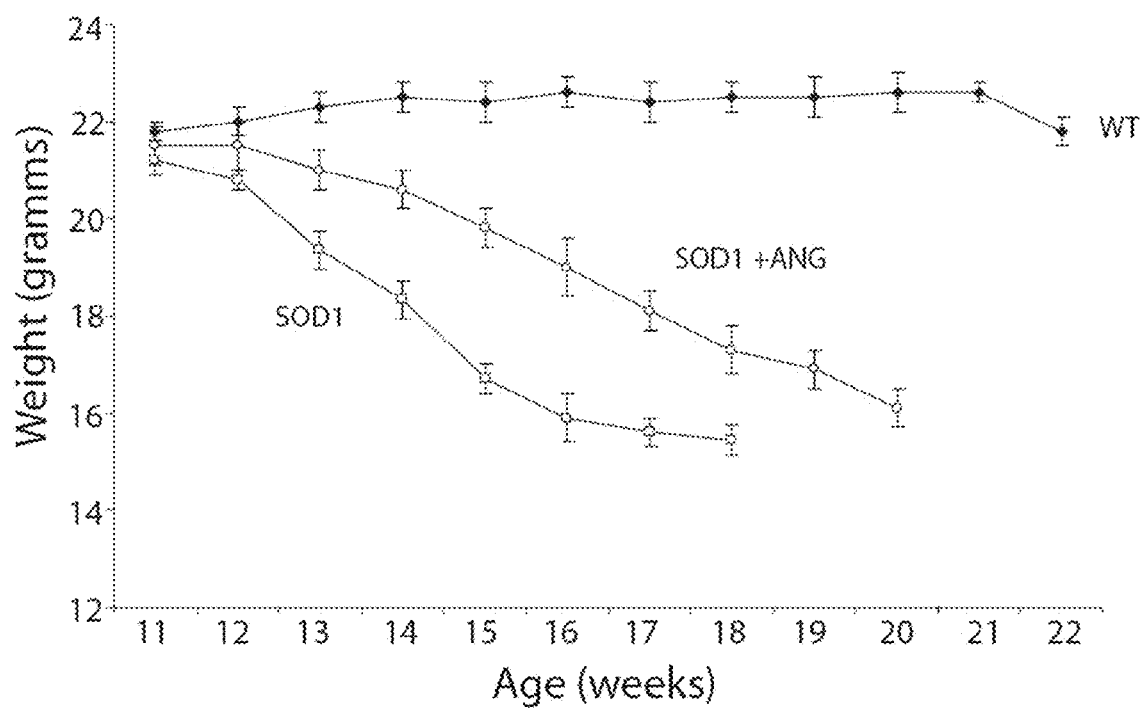
FIG. 5 shows a graph depicting a weight chart of either wt mice (black diamonds) or untreated (white squares) or Ang treated (white circles) SOD1 mice at indicated ages.
Figure 6:
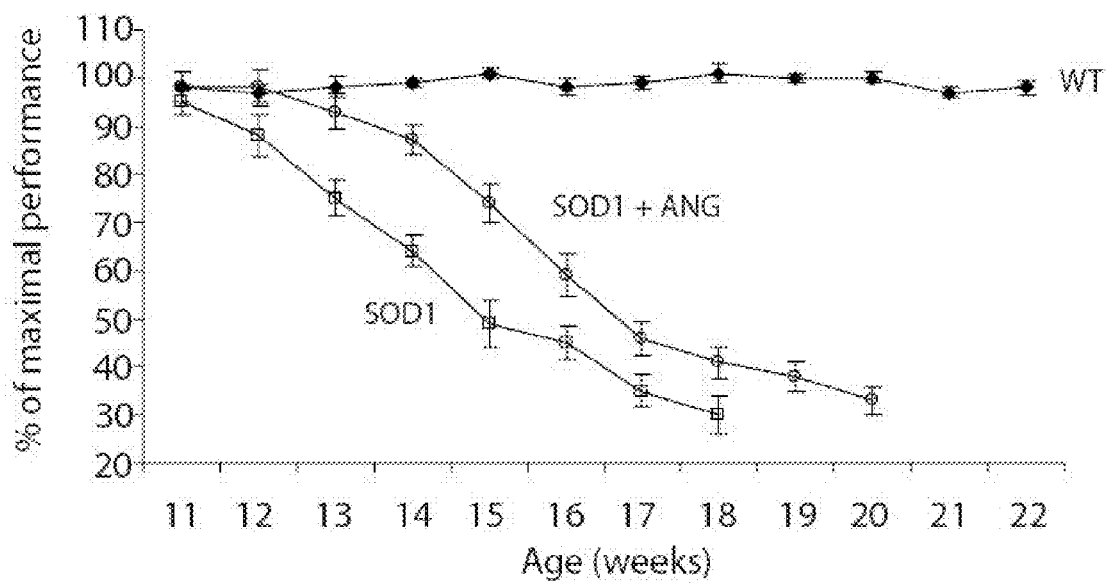
FIG. 6 shows a graph depicting a performance chart using the Paw Grip Endurance test (PaGE) of either wt mice (black diamonds) or untreated (white squares) or Ang treated (white circles) SOD1 mice at indicated ages.
Figure 7:
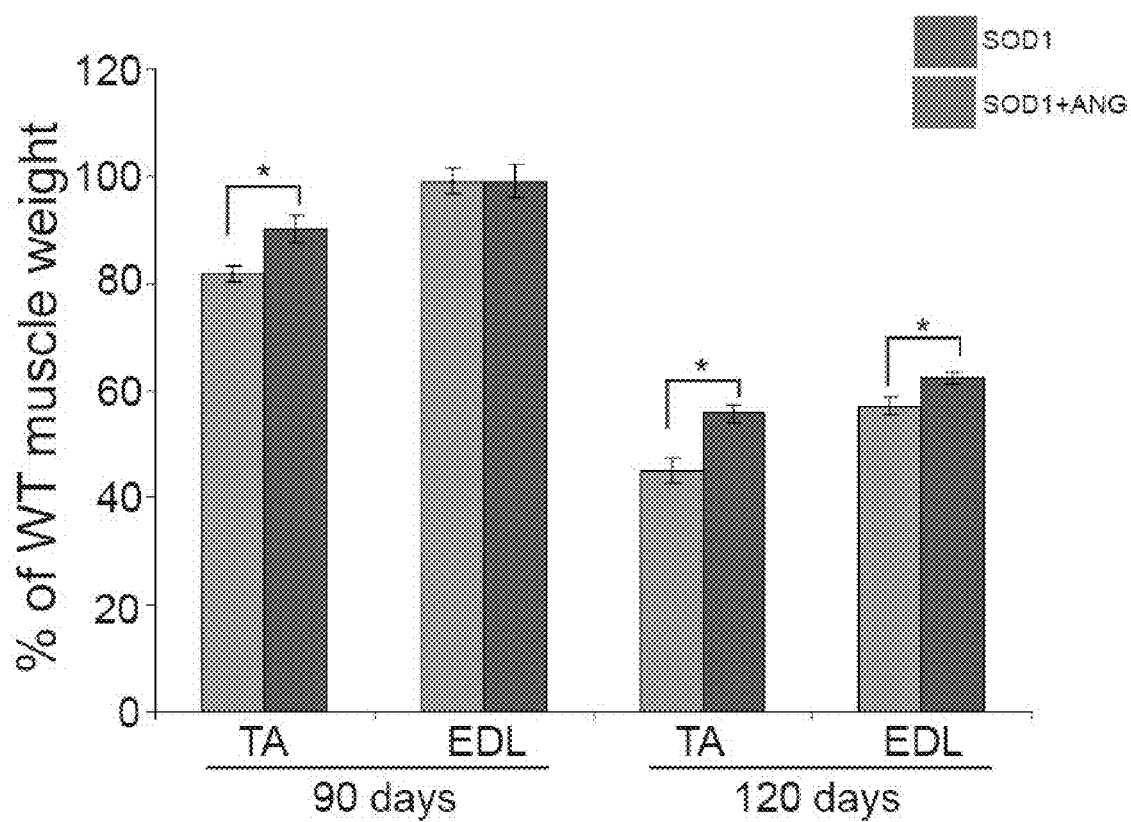
FIG. 7 shows a bar graph depicting the percent muscle weight of untreated (light gray) or Ang treated (dark gray) SOD1 mice as compared to wt mice (set at 100%) of two muscles, tibialis anterior (TA) and extensor digitorum longus (EDL), at 90 days and 120 days, respectively.

In light of the neuroprotective effect of Ang in in-vitro models of motoneuron degeneration, we next examined the effect of treatment with Ang protein in SOD1$^{G93A}$ mice. Animals were treated daily with Ang (1 ug administered i.p.) from 50-days, and sacrificed at the disease end-point, which was defined as the time when they were unable to right themselves in 30 s and had lost 20% body weight. In animals treated from 50-days, (a) neuromuscular function, (b) motoneuron survival and (c) lifespan was monitored and recorded.

a) Neuromuscular Function:

Neuromuscular function of Ang-treated and untreated SOD1$^{G93A}$ mice was examined using footprint tests. Stride length measurements showed that motor weakness was delayed in Ang-treated SOD1$^{G93A}$ mice, such that at 90-days stride length was 60.2 mm (±5.8, n=20) compared to only 41.3 mm (±4.3, n=20, p<0.05) in untreated SOD1$^{G93A}$ littermates. This significant improvement in stride length was also seen at later stages in disease progression, and at 120-days stride length in Ang-treated SOD1$^{G93A}$ mice was 32.1 mm (±2.4, n=20) compared to only 20.4 mm (±2.8, n=20, p<0.05) in untreated SOD1$^{G93A}$ littermates. Ang treatment also delayed the decrease in body weight (FIG. 5), and Paw Grip Endurance test (PaGE test) performance (FIG. 6), that occurred during disease progression in SOD1$^{G93A}$ mice.

b) Motoneuron Survival:

The effect of Ang-treatment on motoneuron survival in the spinal cord was assessed morphologically by counting the number of motoneurons in the sciatic motor pool in lumbar spinal cord of animals at 90-days and the disease end stage. Treatment with Ang significantly increased motoneuron survival in treated SOD1$^{G93A}$ mice at both 90-days and at the disease end stage. In wild-type mice at 90-days, 563 (±11.6 n=6) motoneurons were counted in the segment of the sciatic motor pool examined, compared to only 405 (±12.8, n=5) motoneurons in SOD1$^{G93A}$ mice. In ANG treated SOD1$^{G93A}$ mice, motoneuron survival in the sciatic motor pool was significantly improved such that 498 (±13.7, n=5, p<0.05) motoneurons were counted. At the disease end stage this significant improvement in motoneuron survival in ANG-treated SOD1$^{G93A}$ mice was maintained such that 265 (±15, n=5) motoneurons were counted compared to only 207 (±18.4, n=5, p<0.05) in untreated SOD1$^{G93A}$ littermates. The improvement in motoneuron survival observed in ANG-treated SOD1$^{G93A}$ mice was reflected in the delayed onset of pathological changes in hindlimb muscle histology and reduction in hindlimb muscle weight (Table 4 and FIG. 7).

TABLE 4

Weight of TA and EDL muscles in SOD1 mice

| Muscle | Age(days) | Muscle Weight (mg) | | |
|---|---|---|---|---|
| | | wild-type | SOD1 | SOD1 + ANG |
| EDL | 90 | 10.7(+/−0.3) | 10.6(+/−0.5) | 10.6(+/−0.8) |
| EDL | 120 | 13.1(+/−0.7) | 7.5(+/−0.6)* | 8.2(+/−0.7)* |
| TA | 90 | 57.3(+/−1.1) | 46.9(+/−1.2)* | 51.8(+/−1)* |
| TA | 120 | 63.1(+/−1.9) | 28.5(+/−2.5)* | 35.1(+/−2.3)* |

EDL, extensor digitorum longus;
TA, tibialis anterior;
*p < 0.05 c) Lifespan:

Survival analysis in SOD1$^{G93A}$ mice showed that treatment with Ang from 50-days significantly increased lifespan to 138 days (±2.9, n=11), compared to 127 days (±2.8, n=20. p<0.05) in untreated SOD1$^{G93A}$ mice.

Figure 8:
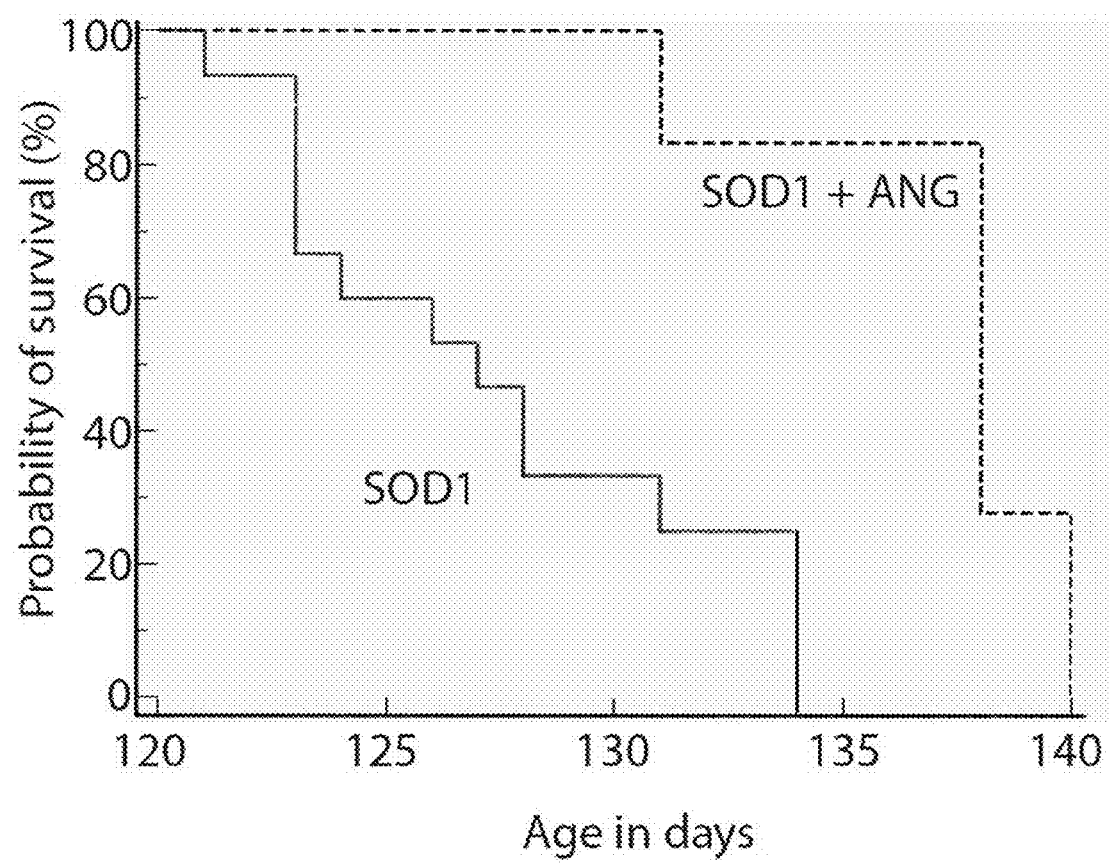
FIG. 8 shows a graph depicting the percentage survival of untreated (SOD1) or Ang-treated (SOD1+ANG) SOD1 mice at indicated ages.

In a second group of mice (n=8), the effect of Ang treatment on lifespan was examined using a more clinically relevant paradigm, where treatment with Ang commenced at a later stage of disease progression (90 days). Interestingly, in mice treated from 90 days, lifespan was also significantly increased (FIG. 8).

The invention is not limited to the embodiments hereinbefore described which may be varied in construction and detail without departing from the spirit of the invention.

The invention claimed is:

1. A method of assessing whether an individual is afflicted with, or genetically predisposed to develop, amyotrophic lateral sclerosis (ALS) or motor neuron disease, or variants thereof, which method comprises a step of assaying a biological sample from the individual for the presence of an angiogenin (ANG) mutations selected from the group consisting of A191T, A107T, A121G, G164A, C189G, and A208G, the position of the mutation calculated from the first nucleotide of the cDNA sequence encoding a full angiogenin transcript (SEQ ID NO:17).

2. The method as claimed in claim 1 in which the variant of amyotrophic lateral sclerosis (ALS) or motor neuron disease is primary lateral sclerosis or spinal muscular atrophy.

3. The method as claimed in claim 1, wherein the ANG mutation is A191T of the full transcript of wild-type angiogenin, the position calculated from the first nucleotide of the cDNA sequence encoding the full angiogenin transcript (SEQ ID NO: 17).

4. The method as claimed in claim 1, wherein the ANG mutation is A107T of the full transcript of wild-type angiogenin, the position calculated from the first nucleotide of the cDNA sequence encoding the full angiogenin transcript (SEQ ID NO: 17).

5. The method as claimed in claim 1, wherein the ANG mutation is A121G of the full transcript of wild-type angiogenin, the position calculated from the first nucleotide of the cDNA sequence encoding the full angiogenin transcript (SEQ ID NO: 17).

6. The method as claimed in claim 1, wherein the ANG mutation is G164A of the full transcript of wild-type angiogenin, the position calculated from the first nucleotide of the cDNA sequence encoding the full angiogenin transcript (SEQ ID NO: 17).

7. The method as claimed in claim 1, wherein the ANG mutation is C189G of the full transcript of wild-type angiogenin, the position calculated from the first nucleotide of the cDNA sequence encoding the full angiogenin transcript (SEQ ID NO: 17).

8. The method as claimed in claim 1, wherein the ANG mutation is A208G of the full transcript of wild-type angiogenin, the position calculated from the first nucleotide of the cDNA sequence encoding the full angiogenin transcript (SEQ ID NO: 17).

9. The method as claimed in claim 1, wherein the step of assaying a biological sample comprises use of an oligonucleotide which is complementary to a sequence of the angiogenin gene which includes at least one of the mutations selected from the group consisting of A191T, A107T, A121G, G164A, C189G, and A208G, the position of the mutation calculated from the first nucleotide of the cDNA sequence encoding a full angiogenin transcript (SEQ ID NO:17).

10. The method as claimed in claim 9, wherein the oligonucleotide is a probe or a primer.

11. The method as claimed in claim 10, wherein the oligonucleotide consists of at least 7, 14, 25, 50, 75, 100, 150, 200, 250, 300, 350, or 400 consecutive nucleotides.

12. The method as claimed in claim 1, wherein the step of assaying a biological sample comprises PCR nucleic acid amplification.

13. The method as claimed in claim 12, wherein the PCR nucleic acid amplification is RT-PCR.

* * * * *

UNITED STATES PATENT AND TRADEMARK OFFICE
CERTIFICATE OF CORRECTION

| | | |
|---|---|---|
| PATENT NO. | : 8,497,070 B2 | Page 1 of 1 |
| APPLICATION NO. | : 12/701790 | |
| DATED | : July 30, 2013 | |
| INVENTOR(S) | : Matt Greenway et al. | |

It is certified that error appears in the above-identified patent and that said Letters Patent is hereby corrected as shown below:

In the Claims:

Claim 1, starting at column 31, line 61, should read:

1.    A method of assessing whether an individual is afflicted with, or genetically predisposed to develop, amyotrophic lateral sclerosis (ALS) or motor neuron disease, or variants thereof, which method comprises a step of assaying a biological sample from the individual for the presence of an angiogenin (ANG) mutation selected from the group consisting of A191T, A107T, A121G, G164A, C189G, and A208G, the position of the mutation calculated from the first nucleotide of the cDNA sequence encoding a full angiogenin transcript (SEQ ID NO: 17).

Signed and Sealed this
Twenty-sixth Day of April, 2016

Michelle K. Lee
*Director of the United States Patent and Trademark Office*

SEQUENCE LISTING

```
<160> NUMBER OF SEQ ID NOS: 19

<210> SEQ ID NO 1
<211> LENGTH: 444
<212> TYPE: DNA
<213> ORGANISM: Homo sapiens
<220> FEATURE:
<223> OTHER INFORMATION: Human Angiogenin Gene with mutation

<400> SEQUENCE: 1
atggtgatgg gcctgggcgt tttgttgttg gtcttcgtgc tgggtctggg tctgacccca      60
ccgaccctgg ctcaggataa ctccaggtac acacacttcc tgacccagca ctatgatgcc     120
aaaccacagg gccgggatga cagatactgt gaaagcatca tgaggagacg gggcctgacc     180
tcaccctgca tagacatcaa cacatttatt catggcaaca agcgcagcat caaggccatc     240
tgtgaaaaca agaatgaaaa ccctcacaga gaaaacctaa gaataagcaa gtcttctttc     300
caggtcacca cttgcaagct acatggaggt tccccctggc ctccatgcca gtaccgagcc     360
acagcggggt tcagaaacgt tgttgttgct tgtgaaaatg gcttacctgt ccacttggat     420
cagtcaattt tccgtcgtcc gtaa                                            444

<210> SEQ ID NO 2
<211> LENGTH: 444
<212> TYPE: DNA
<213> ORGANISM: Homo sapiens
<220> FEATURE:
<223> OTHER INFORMATION: Human Angiogenin Gene with mutation

<400> SEQUENCE: 2
atggtgatgg gcctgggcgt tttgttgttg gtcttcgtgc tgggtctggg tctgacccca      60
ccgaccctgg ctcaggataa ctccaggtac acacacttcc tgaccctgca ctatgatgcc     120
```

| | |
|---|---|
| aaaccacagg gccgggatga cagatactgt gaaagcatca tgaggagacg gggcctgacc | 180 |
| tcaccctgca aagacatcaa cacatttatt catggcaaca agcgcagcat caaggccatc | 240 |
| tgtgaaaaca agaatggaaa ccctcacaga gaaaacctaa gaataagcaa gtcttctttc | 300 |
| caggtcacca cttgcaagct acatggaggt tcccctggc ctccatgcca gtaccgagcc | 360 |
| acagcggggt tcagaaacgt tgttgttgct tgtgaaaatg gcttacctgt ccacttggat | 420 |
| cagtcaattt tccgtcgtcc gtaa | 444 |

<210> SEQ ID NO 3
<211> LENGTH: 444
<212> TYPE: DNA
<213> ORGANISM: Homo sapiens
<220> FEATURE:
<223> OTHER INFORMATION: Human Angiogenin Gene with mutation

<400> SEQUENCE: 3

| | |
|---|---|
| atggtgatgg gcctgggcgt tttgttgttg gtcttcgtgc tgggtctggg tctgacccca | 60 |
| ccgaccctgg ctcaggataa ctccaggtac acacacttcc tgacccagca ctatgatgcc | 120 |
| ataccacagg gccgggatga cagatactgt gaaagcatca tgaggagacg gggcctgacc | 180 |
| tcaccctgca aagacatcaa cacatttatt catggcaaca agcgcagcat caaggccatc | 240 |
| tgtgaaaaca agaatggaaa ccctcacaga gaaaacctaa gaataagcaa gtcttctttc | 300 |
| caggtcacca cttgcaagct acatggaggt tcccctggc ctccatgcca gtaccgagcc | 360 |
| acagcggggt tcagaaacgt tgttgttgct tgtgaaaatg gcttacctgt ccacttggat | 420 |
| cagtcaattt tccgtcgtcc gtaa | 444 |

<210> SEQ ID NO 4
<211> LENGTH: 444
<212> TYPE: DNA
<213> ORGANISM: Homo sapiens
<220> FEATURE:
<223> OTHER INFORMATION: Human Angiogenin Gene with mutation

<400> SEQUENCE: 4

| | |
|---|---|
| atggtgatgg gcctgggcgt tttgttgttg gtcttcgtgc tgggtctggg tctgacccca | 60 |
| ccgaccctgg ctcaggataa ctccaggtac acacacttcc tgacccagca ctatgatgcc | 120 |
| gaaccacagg gccgggatga cagatactgt gaaagcatca tgaggagacg gggcctgacc | 180 |
| tcaccctgca aagacatcaa cacatttatt catggcaaca agcgcagcat caaggccatc | 240 |
| tgtgaaaaca agaatggaaa ccctcacaga gaaaacctaa gaataagcaa gtcttctttc | 300 |
| caggtcacca cttgcaagct acatggaggt tcccctggc ctccatgcca gtaccgagcc | 360 |
| acagcggggt tcagaaacgt tgttgttgct tgtgaaaatg gcttacctgt ccacttggat | 420 |
| cagtcaattt tccgtcgtcc gtaa | 444 |

<210> SEQ ID NO 5
<211> LENGTH: 444
<212> TYPE: DNA
<213> ORGANISM: Homo sapiens
<220> FEATURE:
<223> OTHER INFORMATION: Human Angiogenin Gene with mutation

<400> SEQUENCE: 5

| | |
|---|---|
| atggtgatgg gcctgggcgt tttgttgttg gtcttcgtgc tgggtctggg tctgacccca | 60 |
| ccgaccctgg ctcaggataa ctccaggtac acacacttcc tgacccagca ctatgatgcc | 120 |
| aaaccacagg gccgggatga cagatactgt gaaagcatca tgaagagacg gggcctgacc | 180 |

| | | | | |
|---|---|---|---|---|
| tcaccctgca aagacatcaa cacatttatt catggcaaca agcgcagcat caaggccatc | 240 |
| tgtgaaaaca agaatggaaa ccctcacaga gaaaacctaa gaataagcaa gtcttctttc | 300 |
| caggtcacca cttgcaagct acatggaggt tcccctggc ctccatgcca gtaccgagcc | 360 |
| acagcggggt tcagaaacgt tgttgttgct tgtgaaaatg gcttacctgt ccacttggat | 420 |
| cagtcaattt tccgtcgtcc gtaa | 444 |

<210> SEQ ID NO 6
<211> LENGTH: 444
<212> TYPE: DNA
<213> ORGANISM: Homo sapiens
<220> FEATURE:
<223> OTHER INFORMATION: Human Angiogenin Gene with mutation

<400> SEQUENCE: 6

| | | | | |
|---|---|---|---|---|
| atggtgatgg gcctgggcgt tttgttgttg gtcttcgtgc tgggtctggg tctgacccca | 60 |
| ccgaccctgg ctcaggataa ctccaggtac acacacttcc tgacccagca ctatgatgcc | 120 |
| aaaccacagg gccgggatga cagatactgt gaaagcatca tgaggagacg gggcctgacc | 180 |
| tcaccctgga aagacatcaa cacatttatt catggcaaca agcgcagcat caaggccatc | 240 |
| tgtgaaaaca agaatggaaa ccctcacaga gaaaacctaa gaataagcaa gtcttctttc | 300 |
| caggtcacca cttgcaagct acatggaggt tcccctggc ctccatgcca gtaccgagcc | 360 |
| acagcggggt tcagaaacgt tgttgttgct tgtgaaaatg gcttacctgt ccacttggat | 420 |
| cagtcaattt tccgtcgtcc gtaa | 444 |

<210> SEQ ID NO 7
<211> LENGTH: 444
<212> TYPE: DNA
<213> ORGANISM: Homo sapiens
<220> FEATURE:
<223> OTHER INFORMATION: Human Angiogenin Gene with mutation

<400> SEQUENCE: 7

| | | | | |
|---|---|---|---|---|
| atggtgatgg gcctgggcgt tttgttgttg gtcttcgtgc tgggtctggg tctgacccca | 60 |
| ccgaccctgg ctcaggataa ctccaggtac acacacttcc tgacccagca ctatgatgcc | 120 |
| aaaccacagg gccgggatga cagatactgt gaaagcatca tgaggagacg gggcctgacc | 180 |
| tcaccctgca aagacatcaa cacatttgtt catggcaaca agcgcagcat caaggccatc | 240 |
| tgtgaaaaca agaatggaaa ccctcacaga gaaaacctaa gaataagcaa gtcttctttc | 300 |
| caggtcacca cttgcaagct acatggaggt tcccctggc ctccatgcca gtaccgagcc | 360 |
| acagcggggt tcagaaacgt tgttgttgct tgtgaaaatg gcttacctgt ccacttggat | 420 |
| cagtcaattt tccgtcgtcc gtaa | 444 |

<210> SEQ ID NO 8
<211> LENGTH: 147
<212> TYPE: PRT
<213> ORGANISM: Homo sapiens
<220> FEATURE:
<223> OTHER INFORMATION: Human Angiogenin Protein with mutation

<400> SEQUENCE: 8

Met Val Met Gly Leu Gly Val Leu Leu Val Phe Val Leu Gly Leu
1               5                   10                  15

Gly Leu Thr Pro Pro Thr Leu Ala Gln Asp Asn Ser Arg Tyr Thr His
            20                  25                  30

Phe Leu Thr Gln His Tyr Asp Ala Lys Pro Gln Gly Arg Asp Asp Arg
        35                  40                  45

-continued

```
Tyr Cys Glu Ser Ile Met Arg Arg Gly Leu Thr Ser Pro Cys Ile
        50                  55                  60

Asp Ile Asn Thr Phe Ile His Gly Asn Lys Arg Ser Ile Lys Ala Ile
65                  70                  75                  80

Cys Glu Asn Lys Asn Gly Asn Pro His Arg Glu Asn Leu Arg Ile Ser
                85                  90                  95

Lys Ser Ser Phe Gln Val Thr Thr Cys Lys Leu His Gly Gly Ser Pro
                100                 105                 110

Trp Pro Pro Cys Gln Tyr Arg Ala Thr Ala Gly Phe Arg Asn Val Val
                115                 120                 125

Val Ala Cys Glu Asn Gly Leu Pro Val His Leu Asp Gln Ser Ile Phe
                130                 135                 140

Arg Arg Pro
145

<210> SEQ ID NO 9
<211> LENGTH: 147
<212> TYPE: PRT
<213> ORGANISM: Homo sapiens
<220> FEATURE:
<223> OTHER INFORMATION: Human Angiogenin Protein with mutation

<400> SEQUENCE: 9

Met Val Met Gly Leu Gly Val Leu Leu Leu Val Phe Val Leu Gly Leu
1               5                   10                  15

Gly Leu Thr Pro Pro Thr Leu Ala Gln Asp Asn Ser Arg Tyr Thr His
                20                  25                  30

Phe Leu Thr Leu His Tyr Asp Ala Lys Pro Gln Gly Arg Asp Asp Arg
                35                  40                  45

Tyr Cys Glu Ser Ile Met Arg Arg Gly Leu Thr Ser Pro Cys Lys
        50                  55                  60

Asp Ile Asn Thr Phe Ile His Gly Asn Lys Arg Ser Ile Lys Ala Ile
65                  70                  75                  80

Cys Glu Asn Lys Asn Gly Asn Pro His Arg Glu Asn Leu Arg Ile Ser
                85                  90                  95

Lys Ser Ser Phe Gln Val Thr Thr Cys Lys Leu His Gly Gly Ser Pro
                100                 105                 110

Trp Pro Pro Cys Gln Tyr Arg Ala Thr Ala Gly Phe Arg Asn Val Val
                115                 120                 125

Val Ala Cys Glu Asn Gly Leu Pro Val His Leu Asp Gln Ser Ile Phe
                130                 135                 140

Arg Arg Pro
145

<210> SEQ ID NO 10
<211> LENGTH: 147
<212> TYPE: PRT
<213> ORGANISM: Homo sapiens
<220> FEATURE:
<223> OTHER INFORMATION: Human Angiogenin Protein with mutation

<400> SEQUENCE: 10

Met Val Met Gly Leu Gly Val Leu Leu Leu Val Phe Val Leu Gly Leu
1               5                   10                  15

Gly Leu Thr Pro Pro Thr Leu Ala Gln Asp Asn Ser Arg Tyr Thr His
                20                  25                  30

Phe Leu Thr Gln His Tyr Asp Ala Ile Pro Gln Gly Arg Asp Asp Arg
                35                  40                  45
```

-continued

```
Tyr Cys Glu Ser Ile Met Arg Arg Gly Leu Thr Ser Pro Cys Lys
             50                  55                  60

Asp Ile Asn Thr Phe Ile His Gly Asn Lys Arg Ser Ile Lys Ala Ile
 65                  70                  75                  80

Cys Glu Asn Lys Asn Gly Asn Pro His Arg Glu Asn Leu Arg Ile Ser
                 85                  90                  95

Lys Ser Ser Phe Gln Val Thr Thr Cys Lys Leu His Gly Gly Ser Pro
                100                 105                 110

Trp Pro Pro Cys Gln Tyr Arg Ala Thr Ala Gly Phe Arg Asn Val Val
                115                 120                 125

Val Ala Cys Glu Asn Gly Leu Pro Val His Leu Asp Gln Ser Ile Phe
            130                 135                 140

Arg Arg Pro
145
```

<210> SEQ ID NO 11
<211> LENGTH: 147
<212> TYPE: PRT
<213> ORGANISM: Homo sapiens
<220> FEATURE:
<223> OTHER INFORMATION: Human Angiogenin Protein with mutation

<400> SEQUENCE: 11

```
Met Val Met Gly Leu Gly Val Leu Leu Leu Val Phe Val Leu Gly Leu
  1               5                  10                  15

Gly Leu Thr Pro Pro Thr Leu Ala Gln Asp Asn Ser Arg Tyr Thr His
             20                  25                  30

Phe Leu Thr Gln His Tyr Asp Ala Glu Pro Gln Gly Arg Asp Asp Arg
         35                  40                  45

Tyr Cys Glu Ser Ile Met Arg Arg Gly Leu Thr Ser Pro Cys Lys
             50                  55                  60

Asp Ile Asn Thr Phe Ile His Gly Asn Lys Arg Ser Ile Lys Ala Ile
 65                  70                  75                  80

Cys Glu Asn Lys Asn Gly Asn Pro His Arg Glu Asn Leu Arg Ile Ser
                 85                  90                  95

Lys Ser Ser Phe Gln Val Thr Thr Cys Lys Leu His Gly Gly Ser Pro
                100                 105                 110

Trp Pro Pro Cys Gln Tyr Arg Ala Thr Ala Gly Phe Arg Asn Val Val
                115                 120                 125

Val Ala Cys Glu Asn Gly Leu Pro Val His Leu Asp Gln Ser Ile Phe
            130                 135                 140

Arg Arg Pro
145
```

<210> SEQ ID NO 12
<211> LENGTH: 147
<212> TYPE: PRT
<213> ORGANISM: Homo sapiens
<220> FEATURE:
<223> OTHER INFORMATION: Human Angiogenin Protein with mutation

<400> SEQUENCE: 12

```
Met Val Met Gly Leu Gly Val Leu Leu Leu Val Phe Val Leu Gly Leu
  1               5                  10                  15

Gly Leu Thr Pro Pro Thr Leu Ala Gln Asp Asn Ser Arg Tyr Thr His
             20                  25                  30

Phe Leu Thr Gln His Tyr Asp Ala Lys Pro Gln Gly Arg Asp Asp Arg
         35                  40                  45
```

```
Tyr Cys Glu Ser Ile Met Lys Arg Arg Gly Leu Thr Ser Pro Cys Lys
        50                  55                  60

Asp Ile Asn Thr Phe Ile His Gly Asn Lys Arg Ser Ile Lys Ala Ile
 65                  70                  75                  80

Cys Glu Asn Lys Asn Gly Asn Pro His Arg Glu Asn Leu Arg Ile Ser
                 85                  90                  95

Lys Ser Ser Phe Gln Val Thr Thr Cys Lys Leu His Gly Gly Ser Pro
                100                 105                 110

Trp Pro Pro Cys Gln Tyr Arg Ala Thr Ala Gly Phe Arg Asn Val Val
                115                 120                 125

Val Ala Cys Glu Asn Gly Leu Pro Val His Leu Asp Gln Ser Ile Phe
                130                 135                 140

Arg Arg Pro
145

<210> SEQ ID NO 13
<211> LENGTH: 147
<212> TYPE: PRT
<213> ORGANISM: Homo sapiens
<220> FEATURE:
<223> OTHER INFORMATION: Human Angiogenin Protein with mutation

<400> SEQUENCE: 13

Met Val Met Gly Leu Gly Val Leu Leu Leu Val Phe Val Leu Gly Leu
 1               5                  10                  15

Gly Leu Thr Pro Pro Thr Leu Ala Gln Asp Asn Ser Arg Tyr Thr His
                 20                  25                  30

Phe Leu Thr Gln His Tyr Asp Ala Lys Pro Gln Gly Arg Asp Asp Arg
                 35                  40                  45

Tyr Cys Glu Ser Ile Met Arg Arg Arg Gly Leu Thr Ser Pro Trp Lys
        50                  55                  60

Asp Ile Asn Thr Phe Ile His Gly Asn Lys Arg Ser Ile Lys Ala Ile
 65                  70                  75                  80

Cys Glu Asn Lys Asn Gly Asn Pro His Arg Glu Asn Leu Arg Ile Ser
                 85                  90                  95

Lys Ser Ser Phe Gln Val Thr Thr Cys Lys Leu His Gly Gly Ser Pro
                100                 105                 110

Trp Pro Pro Cys Gln Tyr Arg Ala Thr Ala Gly Phe Arg Asn Val Val
                115                 120                 125

Val Ala Cys Glu Asn Gly Leu Pro Val His Leu Asp Gln Ser Ile Phe
                130                 135                 140

Arg Arg Pro
145

<210> SEQ ID NO 14
<211> LENGTH: 147
<212> TYPE: PRT
<213> ORGANISM: Homo sapiens
<220> FEATURE:
<223> OTHER INFORMATION: Human Angiogenin Protein with mutation

<400> SEQUENCE: 14

Met Val Met Gly Leu Gly Val Leu Leu Leu Val Phe Val Leu Gly Leu
 1               5                  10                  15

Gly Leu Thr Pro Pro Thr Leu Ala Gln Asp Asn Ser Arg Tyr Thr His
                 20                  25                  30

Phe Leu Thr Gln His Tyr Asp Ala Lys Pro Gln Gly Arg Asp Asp Arg
                 35                  40                  45
```

```
Tyr Cys Glu Ser Ile Met Arg Arg Arg Gly Leu Thr Ser Pro Cys Lys
     50                  55                  60

Asp Ile Asn Thr Phe Val His Gly Asn Lys Arg Ser Ile Lys Ala Ile
 65                  70                  75                  80

Cys Glu Asn Lys Asn Gly Asn Pro His Arg Glu Asn Leu Arg Ile Ser
                 85                  90                  95

Lys Ser Ser Phe Gln Val Thr Thr Cys Lys Leu His Gly Gly Ser Pro
            100                 105                 110

Trp Pro Pro Cys Gln Tyr Arg Ala Thr Ala Gly Phe Arg Asn Val Val
        115                 120                 125

Val Ala Cys Glu Asn Gly Leu Pro Val His Leu Asp Gln Ser Ile Phe
    130                 135                 140

Arg Arg Pro
145

<210> SEQ ID NO 15
<211> LENGTH: 123
<212> TYPE: PRT
<213> ORGANISM: Homo sapiens
<220> FEATURE:
<223> OTHER INFORMATION: Human Angiogenin Protein - Wild Type

<400> SEQUENCE: 15

Gln Asp Asn Ser Arg Tyr Thr His Phe Leu Thr Gln His Tyr Asp Ala
 1               5                  10                  15

Lys Pro Gln Gly Arg Asp Asp Arg Tyr Cys Glu Ser Ile Met Arg Arg
             20                  25                  30

Arg Gly Leu Thr Ser Pro Cys Lys Asp Ile Asn Thr Phe Ile His Gly
         35                  40                  45

Asn Lys Arg Ser Ile Lys Ala Ile Cys Glu Asn Lys Asn Gly Asn Pro
 50                  55                  60

His Arg Glu Asn Leu Arg Ile Ser Lys Ser Ser Phe Gln Val Thr Thr
 65                  70                  75                  80

Cys Lys Leu His Gly Gly Ser Pro Trp Pro Pro Cys Gln Tyr Arg Ala
             85                  90                  95

Thr Ala Gly Phe Arg Asn Val Val Val Ala Cys Glu Asn Gly Leu Pro
            100                 105                 110

Val His Leu Asp Gln Ser Ile Phe Arg Arg Pro
            115                 120

<210> SEQ ID NO 16
<211> LENGTH: 147
<212> TYPE: PRT
<213> ORGANISM: Homo sapiens
<220> FEATURE:
<223> OTHER INFORMATION: Human Angiogenin Protein - Wild Type (including
      signal peptide)

<400> SEQUENCE: 16

Met Val Met Gly Leu Gly Val Leu Leu Leu Val Phe Val Leu Gly Leu
 1               5                  10                  15

Gly Leu Thr Pro Pro Thr Leu Ala Gln Asp Asn Ser Arg Tyr Thr His
             20                  25                  30

Phe Leu Thr Gln His Tyr Asp Ala Lys Pro Gln Gly Arg Asp Asp Arg
         35                  40                  45

Tyr Cys Glu Ser Ile Met Arg Arg Arg Gly Leu Thr Ser Pro Cys Lys
 50                  55                  60

Asp Ile Asn Thr Phe Ile His Gly Asn Lys Arg Ser Ile Lys Ala Ile
```

```
                65                  70                  75                  80
            Cys Glu Asn Lys Asn Gly Asn Pro His Arg Glu Asn Leu Arg Ile Ser
                            85                  90                  95
            Lys Ser Ser Phe Gln Val Thr Thr Cys Lys Leu His Gly Gly Ser Pro
                        100                 105                 110
            Trp Pro Pro Cys Gln Tyr Arg Ala Thr Ala Gly Phe Arg Asn Val Val
                    115                 120                 125
            Val Ala Cys Glu Asn Gly Leu Pro Val His Leu Asp Gln Ser Ile Phe
                130                 135                 140
            Arg Arg Pro
            145

<210> SEQ ID NO 17
            <211> LENGTH: 444
            <212> TYPE: DNA
            <213> ORGANISM: Homo sapiens
            <220> FEATURE:
            <223> OTHER INFORMATION: Human Angiogenin gene (including coding for
                  signal peptide)

<400> SEQUENCE: 17
atggtgatgg gcctgggcgt tttgttgttg gtcttcgtgc tgggtctggg tctgacccca      60
ccgaccctgg ctcaggataa ctccaggtac acacacttcc tgacccagca ctatgatgcc     120
aaaccacagg gccgggatga cagatactgt gaaagcatca tgaggagacg gggcctgacc     180
tcaccctgca agacatcaa  cacatttatt catggcaaca agcgcagcat caaggccatc     240
tgtgaaaaca agaatggaaa ccctcacaga gaaaacctaa gaataagcaa gtcttctttc     300
caggtcacca cttgcaagct acatggaggt tcccctggc  ctccatgcca gtaccgagcc     360
acagcggggt tcagaaacgt tgttgttgct tgtgaaaatg gcttacctgt ccacttggat     420
cagtcaattt tccgtcgtcc gtaa                                            444

<210> SEQ ID NO 18
            <211> LENGTH: 20
            <212> TYPE: PRT
            <213> ORGANISM: Homo sapiens

<400> SEQUENCE: 18

Met Val Met Gly Leu Gly Val Leu Leu Leu Val Phe Val Leu Gly Leu
            1               5                   10                  15

Gly Leu Thr Pro
                        20

<210> SEQ ID NO 19
            <211> LENGTH: 5
            <212> TYPE: PRT
            <213> ORGANISM: Homo sapiens

<400> SEQUENCE: 19

Arg Arg Arg Gly Leu
            1               5
```